United States Patent [19]

Stapp

[11] 4,299,998

[45] Nov. 10, 1981

[54] PREPARATION OF ETHERS

[75] Inventor: Paul R. Stapp, Bartlesville, Okla.

[73] Assignee: Phillips Petroleum Co., Bartlesville, Okla.

[21] Appl. No.: 88,702

[22] Filed: Oct. 26, 1979

Related U.S. Application Data

[63] Continuation-in-part of Ser. No. 921,013, Jun. 30, 1978, abandoned.

[51] Int. Cl.$^3$ ............................................. C07C 41/06
[52] U.S. Cl. .................................. 568/697; 568/579; 568/626; 568/662; 568/664; 568/670; 568/678; 568/679; 568/659
[58] Field of Search ............... 568/697, 579, 662–664, 568/670, 678, 679, 659, 626

[56] References Cited

U.S. PATENT DOCUMENTS 4,057,575 11/1977 Klass .................................. 568/594

FOREIGN PATENT DOCUMENTS 1138366 1/1969 United Kingdom ................ 568/697
137508 4/1960 U.S.S.R. ............................ 568/594

*Primary Examiner*—Howard T. Mars

[57] ABSTRACT

Ethers are prepared by reacting olefins and alcohols in the presence of a catalyst system comprising a palladium component and a copper component. The catalyst system can also contain an alkali metal or alkaline earth metal halide with an optional surfactant component also being present in the reaction system. The reaction proceeds in high yield under relatively mild conditions without the presence of a strong acid.

12 Claims, No Drawings

PREPARATION OF ETHERS

This application is a continuation-in-part application of Ser. No. 921,013, filed June 30, 1978, now abandoned.

BACKGROUND OF THE INVENTION

This invention relates to a process for preparing ethers. In another aspect, this invention relates to the preparation of dialkyl ethers by contacting mono-olefin and a mono-alcohol in the presence of a catalyst system. In still another aspect, this invention relates to the preparation of saturated mono-ethers by contacting an olefin and an alcohol in the presence of a palladium- and copper-comprising catalyst system. In another aspect, this invention relates to a process for preparing saturated mono-ethers by contacting an olefin and an alcohol in the presence of a catalyst system comprising palladium, copper, and an alkali metal or alkaline earth metal halide. This invention also relates to a process for preparing ethers by contacting an olefin and an alcohol in the presence of a surfactant and a catalyst system comprising palladium, copper, and an alkali metal or alkaline earth metal halide.

Oxygen-containing compounds, and particularly ethers, are important in forming many valuable articles used commercially. Dialkyl ethers, for example, are known to be valuable anti-knock additives for high octane gasolines. Methyl t-butyl ether is particularly useful as an anti-knock additive due to its low boiling point and high blending octane number. The preparation of ethers by the reaction of olefins with alcohols in the presence of sulfuric acid is a well-known reaction. A process which gives high yields and conversion under relatively mild conditions and does not require the presence of a strong acid such as sulfuric acid, however, would be more desirable.

Accordingly, it is an object of this invention to provide a novel process for the preparation of ethers.

Another object of this invention is to provide a process for the preparation of ethers which proceeds in high yield and under relatively mild conditions without the presence of a strong acid.

Other objects, aspects, and advantages of the invention will be readily apparent to those skilled in the art upon reading the specification and appended claims.

SUMMARY OF THE INVENTION

The present invention provides a method of preparing saturated mono-ethers from alcohols and olefins by contacting a monohydric alcohol and a mono-olefinic compound in the presence of a catalyst system comprising a palladium and a copper component. The reaction is a non-oxidative addition of the alcohol to the olefin to form the saturated, mono-ether.

In another embodiment, the catalyst system of the invention also comprises an optional alkali metal or alkaline earth metal halide component.

The reaction system can also contain an optional surfactant component.

The reaction of the present invention proceeds in high yield under relatively mild conditions without the presence of a strong acid.

DETAILED DESCRIPTION OF THE INVENTION

I. Olefinic Reactant

Any suitable mono-olefin can be used as a reactant for the process of the present invention. Generally, however, the olefins which can be utilized as one of the starting materials of the present process are selected from acyclic mono-olefinic compounds containing from 2–20 carbon atoms per molecule and cyclic olefinic compounds containing from 5–20 carbon atoms per molecule. Suitable olefinic hydrocarbon reactants can be represented by the general formula I:

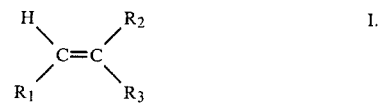

wherein each $R_1$, $R_2$, and $R_3$ are independently selected from the group consisting of hydrogen, alkyl and cycloalkyl radicals and wherein any two of $R_1$, $R_2$, and $R_3$ can be taken together to form an alkylene radical thus forming a cyclic system. The term "olefinic carbon-carbon double bond" as used herein is not meant to include those carbon-carbon double bonds which are part of an aromatic carbocyclic system of alternating single and double bonds. The hydrocarbyl radicals described above can also contain substituents that are substantially inert under the reaction conditions. Such substituents include aryl and alkoxy radicals.

Examples of suitable mono-olefinic compounds include: ethylene, propylene, 1-butene, 2-butene, isobutylene, 1-pentene, 2-pentene, 1-hexene, 2-hexene, 3-hexene, 1-octene, 1-decene, 1-dodecene, 1-hexadecene, 1-octadecene, 1-eicosene, vinyl cyclohexane, cyclopentene, cyclohexene, cycloheptene, cyclooctene, cyclododecene, 3,3-dimethyl-1-butene, and the like, and mixtures thereof.

For reasons of availability and value of the resulting ether products, the currently preferred olefinic starting materials for the reaction of this invention are acyclic mono-olefinic compounds containing from 2 to 8 carbon atoms per molecule.

II. Alcohol Reactant

Any suitable monohydric alcohol can be used as a reactant for the process of the present invention. Generally, however, the alcohol which can be utilized as a starting material in the process of this invention can be represented by the following general formula II:

wherein $R_4$ is selected from alkyl radicals containing 1 to about 20 carbon atoms per radical, cycloalkyl radicals containing 5 to about 10 carbon atoms per radical, and aralkyl radicals containing 7 to about 20 carbon atoms per radical. $R_4$ can also contain substituents such as alkoxy radicals that are substantially inert under the reaction conditions.

Examples of alcohols which can be utilized in the reaction with the mono-olefinic materials previously described include methyl alcohol, ethyl alcohol, propyl alcohol, isopropyl alcohol, n-butyl alcohol, sec-butyl alcohol, n-amyl alcohol, n-hexyl alcohol, n-octyl alcohol, benzyl alcohol, cyclohexanol, 3-phenyl-1-propanol, 2-methoxy-1-propanol, and the like, and mixtures thereof.

For reasons of availability, cost, and value of the products, the currently preferred monohydric alcohol reactants are the alkyl monohydric alcohols containing 1 to about 8 carbon atoms per molecule.

The molar ratio of the alcohol group (—OH) to the olefinic group (—C=C— double bond) can be within the range of about 20:1 to about 1:20. It is generally preferred that the molar ratio of alcohol group to olefinic group be from 0.5:1 to 10:1.

III. Catalyst System

The catalyst utilized according to the present invention for the reaction of monohydric alcohols with mono-olefins is made up of the following components: (1) a palladium component, (2) a copper component, and (3) optionally, an alkali metal or alkaline earth metal halide component. In addition, a surfactant is an optional component of the system.

(1) Palladium Component

The palladium component of the catalyst system of the instant invention can be palladium metal such as finely divided palladium powder or a palladium compound. Examples of suitable palladium compounds include allyl palladium chloride dimer $[C_3H_5PdCl]_2$, dichlorobis (triphenylphosphine) palladium(II), palladium(II) acetate, palladium(II) acetylacetonate, tetrakis (triphenylphosphine) palladium(0), palladium(II) chloride, palladium(II) iodide, palladium(II) nitrate, and the like. Mixtures of the above palladium compounds can also be utilized as the palladium component of the instant catalyst system if so desired.

(2) Copper Component

The copper component of the instant catalyst system can be provided by utilizing a cuprous or cupric compound or mixture thereof. A wide variety of copper compounds can be utilized to provide the copper component of the instant catalyst system. Specific examples of suitable copper compounds include copper(I) acetate, copper(II) acetylacetonate, copper(I) bromide, copper(I) chloride, copper(II) chloride, copper(I) iodide, copper(II) nitrate, and the like. Mixtures of suitable copper compounds can also be employed to provide the copper component of the instant catalyst system if so desired.

(3) Alkali Metal or Alkaline Earth Metal Halide

The third component of the catalyst system of the instant invention is an optional component and it is currently preferred that it be present. This component is a halide of an alkali metal or an alkaline earth metal. Specific examples of suitable alkali metal halides include lithium chloride, sodium chloride, potassium chloride, rubidium chloride, cesium chloride, lithium bromide, sodium bromide, potassium bromide, sodium iodide, and the like. Examples of suitable alkaline earth metal halides include calcium chloride, barium chloride, strontium chloride, magnesium chloride, beryllium chloride, calcium bromide, barium bromide, calcium iodide, and the like. Mixtures of the above metal halides can be employed as the third component of the catalyst system if so desired.

The ratios of the various catalyst components can be expressed in terms of a molar ratio of copper to palladium and a molar ratio of halide ion derived from the alkali metal or alkaline earth metal halide to palladium. The molar ratio of copper component to palladium component in the instant catalyst system is broadly from about 1/1 up to about 200/1 and preferably from about 2/1 up to about 50/1. The molar ratio of halide ion derived from the alkali metal or alkaline earth metal halide to palladium is broadly from about 5/1 to about 1,000/1 and preferably from about 10/1 up to about 400/1.

The amount of catalyst employed according to the instant invention can be expressed in terms of the molar ratio of olefinic reactant to palladium component of the catalyst system. Broadly, the molar ratio of olefinic reactant to palladium component is from about 5/1 up to about 1,000/1 and preferably from about 10/1 up to about 250/1.

Another component of the reaction system according to the present invention is a surfactant. This component is considered to be an optional component, but it is currently preferred that a surfactant be present. The presence of a surfactant is expected to be of particular value when the olefin and alcohol starting materials are not completely miscible and the surfactant can act as a phase transfer agent or when some of the catalyst components have relatively low solubility in one or more of the starting materials.

Although any compound that exhibits surface-active properties can be used as a surfactant in this invention, it is currently preferred that the surfactant be selected from one of the five following groups.

(A) Quaternary ammonium salts of the general formula $(R''')_4N^+X^-$ wherein $R'''$ is an alkyl radical of from 1 to 20 carbon atoms and wherein the total number of carbon atoms in said quaternary ammonium salt is from 8 to 30 carbon atoms broadly and preferably from 16 to 22 carbon atoms; and wherein $X^-$ is selected from the group consisting of $Br^-$, $Cl^-$, $I^-$, $F^-$, $R'''CO_2^-$, $QSO_3^-$, $HSO_4^-$, wherein Q is an aryl or alkaryl radical of 6 to 10 carbon atoms. Specific examples of quaternary ammonium salts according to the general formula given above include cetyltrimethylammonium bromide, tetraheptylammonium bromide, cetyltrimethylammonium stearate, benzyltributylammonium chloride, benzyltriethylammonium bromide, benzyltrimethylammonium bromide, phenyltrimethylammonium bromide, phenyltrimethylammonium iodide, tetrabutylammonium bromide, tetrabutylammonium chloride, tetrabutylammonium hydrogen sulfate, tetrabutylammonium iodide, tetraethylammonium bromide, tetrabutylammonium fluoride, tetrabutylammonium tetrafluoroborate, and the like.

(B) Alkali metal alkyl sulfates of the general formula $R'^vOSO_3M$ wherein $R'^v$ is an alkyl radical of from 10 to about 20 carbon atoms and wherein M is an alkali metal. Examples of suitable compounds according to the general formula for the alkali metal alkyl sulfates include lithium decylsulfate, potassium dodecylsulfate, sodium dodecylsulfate, sodium hexadecylsulfate, potassium hexadecylsulfate, rubidium dodecylsulfate, cesium dodecylsulfate, sodium octadecylsulfate, potassium octadecylsulfate, potassium eicosylsulfate, sodium eicosylsulfate, and the like.

(C) Alkali metal salts of alkanoic acids of the general formula $R'^vCO_2M$ wherein $R'^v$ and M have the same meaning as given above for the compounds of (B). Examples of suitable alkali metal salts of alkanoic acids include lithium decanoate, sodium dodecanoate, potassium dodecanoate, rubidium dodecanoate, cesium dodecanoate, sodium hexadecanoate, potassium hexadecanoate, sodium octadecanoate, potassium octadecanoate, sodium eicosanoate, potassium eicosanoate, and the like.

(D) Alkali metal salts of alkaryl sulfonic acids of the general formula

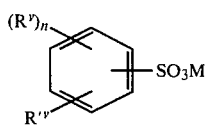

wherein R'$^v$ and M have the same meaning as given above and wherein R$^y$ is an alkyl radical of 1 to 4 carbon atoms and wherein n is 0 or an integer of from 1 to 4. Specific examples of compounds within the (D) group include sodium dodecylbenzenesulfonate, potassium dodecylbenzenesulfonate, lithium dodecylbenzenesulfonate, sodium tetradecylbenzenesulfonate, potassium hexadecylbenzenesulfonate, rubidium dodecylbenzenesulfonate, cesium dodecylbenzenesulfonate, sodium eicosylbenzenesulfonate, potassium dodecyltoluenesulfonate, sodium dodecylxylenesulfonate, and the like.

(E) 1-Alkyl pyridinium salts of the general formula

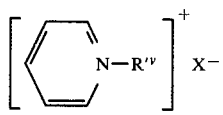

wherein R'$^v$ and X$^-$ have the same meaning as described above. Examples of suitable 1-alkyl pyridinium salts include 1-dodecylpyridinium para-toluenesulfonate, 1-dodecylpyridinium chloride, 1-hexadecylpyridinium chloride, 1-hexadecylpyridinium para-toluenesulfonate, 1-decylpyridinium chloride, 1-hexadecylpyridinium bromide, 1-tetradecylpyridinium chloride, 1-octadecylpyridinium chloride, 1-eicosylpyridinium chloride, 1-octadecylpyridinium benzenesulfonate, and the like.

The amount of surfactant compound selected from groups (A) through (E) which is utilized according to the instant invention can be expressed in terms of a mole ratio based on the palladium component of the catalyst system. Broadly, the mole ratio surfactant to palladium compound will be from 0.01/1 to 10/1 and preferably from 0.1/1 to 3/1.

IV. Reaction Conditions

The process of this invention can be carried out at a reaction temperature that is within the broad range of about 20° C. to about 200° C. (68°–392° F.) and preferably from about 60° C. to about 150° C. (140°–302° F.).

The pressure utilized in the practice of this invention can be autogenous or can range up to as much as about 5000 psig (34470 kPa) with the pressure being provided by the introduction of a substantially inert gas such as nitrogen into the reaction zone.

The time employed for the reaction according to the instant invention in a batch reaction can vary over a wide range and will to some extent depend on the desired degree of conversion of the reactant. Generally, a time period such as from 30 minutes to eight hours will be employed in the instant invention.

Intimate contact of the reactants and catalyst is expected to be of benefit in the reaction of this invention and conventional means of good mixing by stirring, shaking, and the like can be employed as taught in the prior art.

The charge order of the reaction components and catalyst components is not particularly critical in the process of the instant invention.

The process of the instant invention can be carried out in either a batch or continuous process.

The reaction of this invention can be carried out in the absence of any added diluents. In this case, an excess of one of the reactants will generally be used to act as a diluent. However, it is generally preferred that an organic diluent that is substantially inert under the reaction conditions be present. The reactants and catalyst should have sufficient solubility in the organic diluent to allow the reaction to occur at a reasonable rate. Generally speaking, suitable compounds can be found in the classes of compounds described as alkanes, cycloalkanes, aromatic hydrocarbons or alkyl-substituted aromatic hydrocarbons, and halogenated aromatic compounds. Specific examples of suitable organic diluents include cyclohexane, hexane, benzene, toluene, chlorobenzene, bromobenzene, 1,2,4-trichlorobenzene, ortho-dichlorobenzene, sulfolane, orthoxylene, para-xylene, meta-xylene, methylcyclopentane, and the like. Mixtures of the above organic diluents may be utilized in some cases as desired. Generally speaking, the choice of the organic diluents can be often determined based on the difference in boiling points expected between the product of the addition reaction and the organic diluent so as to facilitate separation of the components of the reaction mixture.

The amount of organic diluent based on the starting monohydric alcohol reactant can vary over a wide range and a suitable broad range includes from 0.01/1 to 200/1 volumes of organic diluent per volume of alcohol reactant and preferably from 0.1/1 to 50/1 volumes of organic diluent per volume of alcohol reactant.

In order to avoid the formation of products other than the saturated mono-ethers of this invention, water and oxygen are excluded from the reaction mixture during the reaction period.

V. Reaction Mixture Workup

A variety of methods can be utilized to recover the reaction product, unreacted starting materials, catalyst, and diluent, if used. For example, one method of reaction mixture workup can involve fractional distillation of the entire reaction mixture to separate the components into various fractions and the distillation kettle bottoms can be recycled to the reaction zone as that portion containing essentially all of the catalyst system for the reaction.

Another method of treating the reaction mixture is to contact the entire mixture with a lower alkane such as n-pentane and water and then separate the aqueous phase to recover the products and any unreacted reactants.

VI. Product Utility

As indicated earlier, the reaction of this invention provides a process for the reaction of mono-olefins and mono-alcohols to yield saturated mono-ethers. The saturated mono-ether is produced by the non-oxidative addition of the mono-olefin and mono-alcohol. One valuable ether product which can be formed by the reaction of this invention is methyl t-butyl ether, which is illustrated by the following reaction:

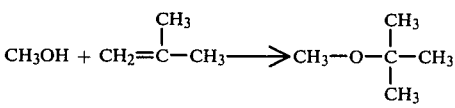

Methyl t-butyl ether is known to be a valuable antiknock additive for high octane gasoline.

It is readily apparent that a wide variety of symmetrical and asymmetrical ethers can be prepared by the process of this invention by the use of various olefins and alcohols.

For example, the reaction of propylene and ethyl alcohol will yield ethyl 2-propyl ether, 1-butene and propyl alcohol will yield 2-butyl 1-propyl ether, 1-decene and n-octyl alcohol will yield 2-decyl 1-octyl ether, cyclohexene and methyl alcohol will yield cyclohexyl methyl ether, isobutylene and cyclohexanol will yield cyclohexyl t-butyl ether, and 1-pentene and benzyl alcohol will yield benzyl 2-pentyl ether.

The invention is further illustrated by the following example:

VII. Example

A 250 ml Fischer-Porter aerosol compatibility bottle equipped with a magnetic stirrer was charged with 0.9 g (5 mmoles) palladium chloride, 3.4 g (20 mmoles) cupric chloride dihydrate, 4.3 g (100 mmole) lithium chloride, 0.7 g (1.8 mmoles) cetyltrimethylammonium bromide, 50 ml (39.6 g, 1.238 moles) methanol, 50 ml chlorobenzene, and 11.7 g (208.9 mmoles) isobutylene (in the vapor phase). The bottle was placed in an oil bath, heated to 105° C. and maintained at that temperature for a reaction time of about 4¾ hours. The reactor was cooled and vented, and the reaction mixture was analyzed by gas-liquid chromatography (glc). The results of the analysis indicated that 206.7 mmoles of methyl t-butyl ether was present for a yield of 99 mole percent based on the amount of isobutylene charged to the reactor. Identification of the product was achieved by a glc-mass spectral analysis.

While a specific embodiment of the invention has been described for illustrative purposes, the invention is not limited thereto. Various other modifications and embodiments of the invention will be apparent to those skilled in the art in view of this disclosure. Such modifications or embodiments are within the scope and spirit of this disclosure.

I claim:

1. A process for the preparation of saturated mono-ethers by reacting a mono-olefin and a monohydric alcohol which comprises contacting in the absence of water and oxygen
   (a) a mono-olefinic compound with
   (b) a monohydric alcohol, in the presence of
   (c) a catalyst system comprising a palladium component, a copper component, and an alkali metal or alkaline earth metal halide component under reaction conditions of temperature and pressure sufficient to form a saturated mono-ether product.

2. A process in accordance with claim 1 wherein said contacting also takes place in the presence of a surfactant.

3. A process in accordance with claim 2 wherein said surfactant is selected from the group of:
   (1) quaternary ammonium salts of the general formula $(R''')_4N^+X^-$,
   (2) alkali metal alkyl sulfates of the general formula $R'^vOSO_3M$,
   (3) alkali metal salts of alkanoic acids of the general formula $R'^vCO_2M$,
   (4) alkali metal salts of alkaryl sulfonic acids of the general formula

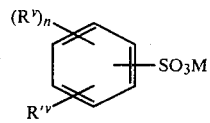

(5) 1-alkyl pyridinium salts of the general formula

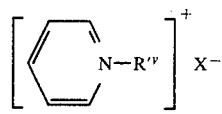

wherein $R'''$ is an alkyl radical of from 1 to 20 carbon atoms and wherein the total number of carbon atoms in said quaternary ammonium salt is from about 8 to about 30 carbon atoms; $X^-$ is selected from the group consisting of $Br^-$, $Cl^-$, $I^-$, $F^-$, $R'''CO_2^-$, $QSO_3^-$, $BF_4^-$, $HSO_4^-$ wherein Q is an aryl or alkaryl radical of 6 to 10 carbon atoms; $R'^v$ is an alkyl radical of from 10 to about 20 carbon atoms; M is an alkali metal; $R^v$ is an alkyl radical of 1 to 4 carbon atoms and wherein n is 0 or an integer of from 1 to 4.

4. A process in accordance with claim 1 wherein said mono-olefin is selected from the group consisting of:
   (a) acyclic mono-olefinic compounds containing from 2-20 carbon atoms per molecule, and
   (b) cyclic mono-olefinic compounds containing 5-20 carbon atoms per molecule; and
   said monohydric alcohol has the general formula $R_4OH$ wherein $R_4$ is selected from the group consisting of:
   (1) alkyl radicals containing from 1 to about 20 carbon atoms per radical,
   (2) cycloalkyl radicals containing 5 to about 10 carbon atoms per radical, and
   (3) aralkyl radicals containing 7 to 20 carbon atoms per radical.

5. A process in accordance with claim 4 wherein said olefin is an acyclic mono-olefinic compound containing from 2 to 8 carbon atoms per molecule and said alcohol is an alkyl monohydric alcohol containing 1 to about 8 carbon atoms per molecule.

6. A process in accordance with claim 1 wherein said contacting takes place at a temperature of about 20° C. to about 200° C. under autogenous pressure.

7. A process in accordance with claim 1 wherein the molar ratio of the alcohol group to the olefinic group is in the range of about 20:1 to about 1:20,
   the molar ratio of the olefinic reactant to palladium of the catalyst system is in the range of about 5:1 to about 1,000:1, and
   the molar ratio of copper to palladium in the catalyst system is from about 1:1 to about 200:1.

8. A process in accordance with claim 7 wherein the molar ratio of the alcohol group to the olefinic group is in the range of about 0.5:1 to 10:1,
   the molar ratio of the olefinic reactant to palladium of the catalyst system is 10:1 to about 250:1, and
   the molar ratio of the copper to palladium in the catalyst system is from about 2:1 to about 50:1.

9. A process in accordance with claim 1 wherein the molar ratio of halide ion derived from the alkali metal or alkaline earth metal halide to palladium in the catalyst system is from about 5:1 to about 1,000:1.

10. A process in accordance with claim 2 wherein the molar ratio of the surfactant to palladium in the catalyst system is in the range of about 0.01:1 to about 10:1.

11. A process in accordance with claim 1 wherein said olefinic compound is isobutylene and said monohydric alcohol is methanol.

12. A process for the preparation of methyl t-butyl ether which comprises contacting in the absence of water and oxygen:
 (a) isobutylene and
 (b) methanol, in the presence of
 (c) a catalyst system comprising palladium chloride, cupric chloride, and lithium chloride, and
 (d) cetyltrimethylammonium bromide, under such conditions of temperature and pressure as to form methyl t-butyl ether.

* * * * *